United States Patent [19]

Dunbar et al.

[11] Patent Number: 4,684,398

[45] Date of Patent: Aug. 4, 1987

[54] HERBICIDAL CYANOGUANIDINES AND CYANOISOTHIOUREAS

[75] Inventors: Joseph E. Dunbar; David M. Hedstrand, both of Midland, Mich.

[73] Assignee: The Dow Chemical Company, Midland, Mich.

[21] Appl. No.: 840,357

[22] Filed: Mar. 17, 1986

Related U.S. Application Data

[63] Continuation-in-part of Ser. No. 641,810, Aug. 17, 1984.

[51] Int. Cl.$^4$ .................... A01N 31/06; A01N 33/04; C07C 125/08

[52] U.S. Cl. .......................................... 71/98; 71/121; 564/105

[58] Field of Search ..................... 564/105; 71/98, 121

[56] References Cited

U.S. PATENT DOCUMENTS 2,780,535  2/1957  Snyder ................................... 71/98
3,542,873  11/1970  Faith ..................................... 71/121

Primary Examiner—Anton H. Sutto
Attorney, Agent, or Firm—S. Preston Jones; Ronald G. Brookens

[57] ABSTRACT

Disclosed are certain cyanoguanidines and cyanoisothioureas that are useful as herbicides.

26 Claims, No Drawings

HERBICIDAL CYANOGUANIDINES AND CYANOISOTHIOUREAS

CROSS REFERENCE TO RELATED APPLICATION

This application is a continuation-in-part of application Ser. No. 641,810, filed Aug. 17, 1984.

BACKGROUND OF THE INVENTION

The present invention is directed to a method of controlling plants by applying certain herbicides to said plants. The herbicides disclosed herein are certain cyanoguanidines and carbaminidothioates.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

SUMMARY OF THE INVENTION

The present invention is directed to a method for controlling the growth of plants comprising applying to said plants or plant loci a herbicidally effective amount of a compound of the formula:

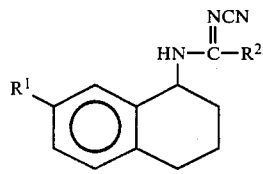
(I)

wherein $R^1$ is hydrogen or methoxy; and $R^2$ is methylthio; alkylamino of the formula

wherein $R^3$ is a straight chain, branched, or cyclic alkyl moiety of 1 to 12 carbon atoms; or alkenylamino of the formula:

wherein $R^4$ is a straight chain or branched alkenyl moiety of 3 to 12 carbon atoms.

Certain of the compounds of formula I have animal growth promoting activity and are taught and claimed in copending application Ser. No. 641,810.

Certain other compounds of formula I are novel and the present invention is also directed to these compounds. Certain novel compounds of the present invention are the compounds of formula I having the proviso that when $R^1$ is hydrogen then $R^2$ cannot be methylthio, alkylamino of 1 to 3 carbon atoms, or alkenylamino of 3 carbon atoms. Also novel is the cyclopropyl derivative (i.e., the compound of Example 13).

As used herein, the term "herbicide" means a compound or composition which controls the growth of plants. By the term "herbicidally effective amount" is meant any amount of such compound or composition which controls or causes a controlling effect upon the growth of plants. By "plants" is meant germinant seeds, emerging seedlings and established vegetation, including roots and above-ground portions. As used herein, the term "control" or "controlling" includes all deviations from natural development, such as killing, retardation, defoliation, desiccation, regulation, stunting, tillering, leaf burn, dwarfing and the like.

The present invention is also directed to herbicidal compositions comprising a herbicidally effective amount of the compound of formula I and an inert diluent carrier.

In the compounds of the present invention and in the methods and compositions of the present invention, it is preferred that $R^3$ is $C_1-C_4$ alkyl and that $R^4$ is $C_3-C_4$ alkenyl.

DETAILED DESCRIPTION OF THE INVENTION

The herbicide compounds disclosed in the present invention can be prepared as described hereinafter.

N'-cyano-N-(1,2,3,4-tetrahydro-1-naphthyl)-S-methylisothiourea, is prepared by contacting and mixing 1,2,3,4-tetrahydro-1-naphthylamine and dimethyl cyanodithioiminocarbonate in the presence of a suitable organic solvent such as methanol, ethanol, propanol or acetonitrile under conditions at which the desired compound is formed. For example, the reaction proceeds at a temperature of between about 0° C. and 80° C. Typically, equimolar amounts of the reactants are employed, however, the molar proportion of the reactants is not critical. The reaction is illustrated as follows:

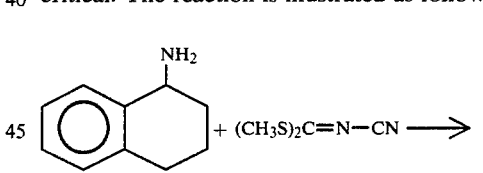

To prepare N'-cyano-N-(7-methoxy-1,2,3,4-tetrahydro-1-naphthyl)-S-methylisothiourea, 7-methoxy-1-tetralone is reacted with hydroxylamine in a suitable solvent such as methanol, ethanol, propanol, or acetonitrile under conditions at which 1,2,3,4-tetrahydro-1-isonitroso-7-methoxynaphthalene is formed. The isonitroso compound thus formed is then reacted with hydrogen in the presence of a suitable catalyst such as 5 percent palladium on charcoal (Pd/C) under conditions at which 7-methoxy-1,2,3,4-tetrahydro-1-naphthylamine is formed.

The amine compound thus formed is then reacted with dimethyl cyanodithioiminocarbonate in the presence of a suitable organic solvent under conditions at which the desired compound is formed. The reaction sequence is illustrated as follows:

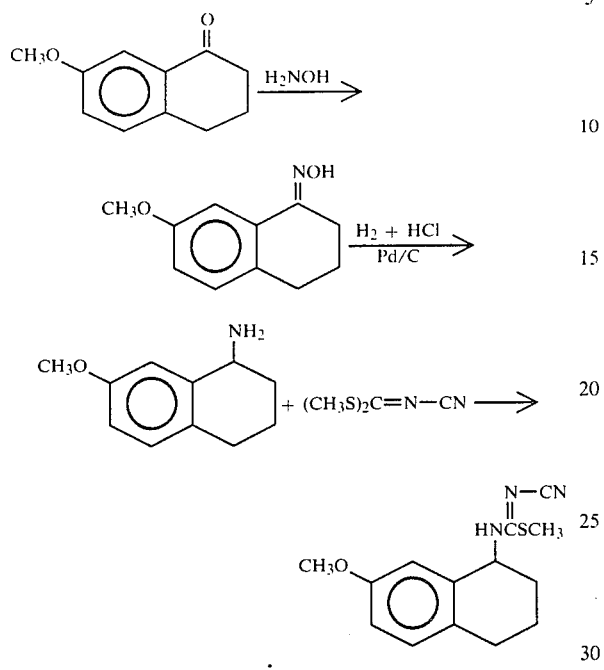

To prepare the alkyl and alkenyl substituted cyanoguanidine derivatives, N'-cyano-N-(1,2,3,4-tetrahydro-1-naphthyl)-S-methylisothiourea or N'-cyano-N-(7-methoxy-1,2,3,4-tetrahydro-1-naphthyl)-S-methylisothiourea is reacted with an appropriate alkylamine or alkenylamine of the formula $H_2NR^3$ or $H_2NR^4$ wherein $R^3$ and $R^4$ as previously defined in an appropriate solvent such as ethanol, acetonitrile, methanol, or propanol under conditions at which the desired compound is formed. For example, the reaction proceeds when the reaction mixture is heated at about 70° C. to 130° C. for about 8 hours to 2 weeks. The desired product can then be recovered using conventional procedures. The reaction can be illustrated as follows:

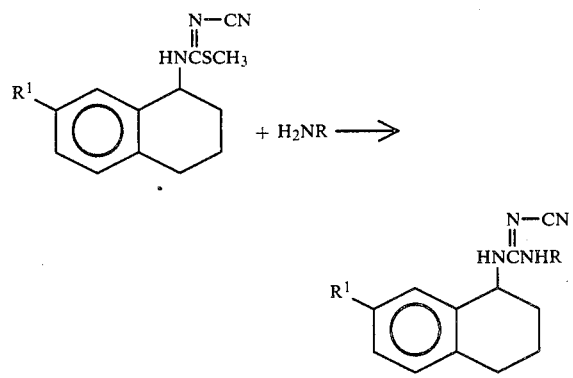

wherein R represents alkyl ($C_1$ to $C_{12}$), or alkenyl ($C_3$ to $C_{12}$), and $R^1$ is as previously defined.

Alternately, the alkyl and alkenyl substituted cyanoguanidines can be made as illustrated in the following reaction scheme:

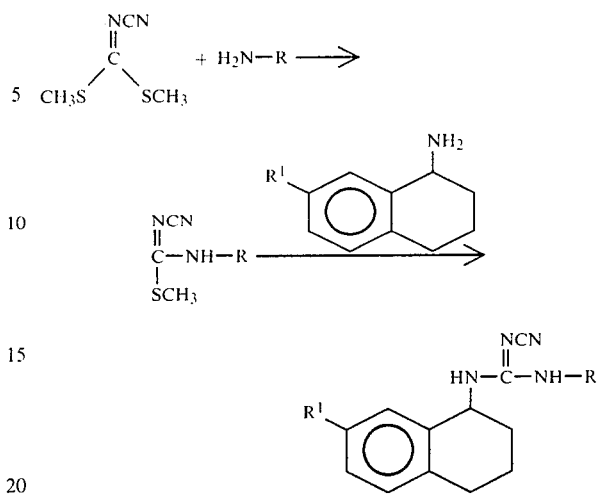

The present invention is further illustrated by the following examples; however, these examples should not be interpreted as a limitation upon the scope of the present invention.

EXAMPLE 1

Preparation of N'-cyano-N-(1,2,3,4-tetrahydro-1-naphthyl)-S-methylisothiourea, represented by the formula:

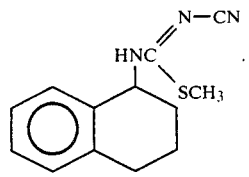

A solution of 73.6 grams (g) of 1,2,3,4-tetrahydro-1-naphthylamine in 75 milliliters (ml) of ethanol was slowly added to a solution of 73.1 g of dimethyl cyanodithioiminocarbonate in 200 ml of ethanol, keeping the temperature between 5° C. and 7° C. by means of an ice bath. After the addition was complete, the reaction flask was kept in the ice bath for 30 minutes, removed from the ice bath and allowed to stand at room temperature for 3 hours during which time 103.5 g of N'-cyano-N-(1,2,3,4-tetrahydro-1-naphthyl)-S-methylisothiourea precipitated as a white, crystalline solid, melting point (mp) 143°–144° C.

| Analysis | C | H | N |
|---|---|---|---|
| Calculated for $C_{13}H_{15}N_3S$: | 63.64 | 6.16 | 17.13 |
| Found: | 63.7 | 6.01 | 17.26 |

EXAMPLE 2

Preparation of 1,2,3,4-tetrahydro-1-isonitroso-7-methoxynaphthalene, represented by the formula:

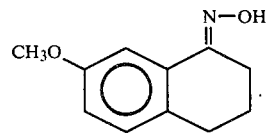

To a stirred mixture of 25.0 g of 7-methoxy-1-tetralone and 15 g of hydroxylamine hydrochloride in 200 ml of ethanol was added a solution of 30 g of sodium acetate in 60 ml of hot water. The reaction mixture was heated on the steam bath for 30 minutes and then diluted with water until the mixture became turbid. The reaction mixture was then allowed to cool to room temperature to give a solid precipitate, which was collected on a filter and recrystallized from aqueous ethanol to give 1,2,3,4-tetrahydro-1-isonitroso-7-methoxynaphthalene as 27.0 g of off-white crystals, mp 88°–90°.

Anal. Calcd for $C_{11}H_{13}NO_2$: C, 69.09; H, 6.85; N, 7.33. Found: C, 69.03; H, 6.93; N, 7.35.

EXAMPLE 3

Preparation of 7-methoxy-1,2,3,4-Tetrahydro-1-naphthylamine, represented by the formula:

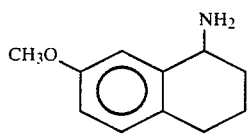

To a suspension of 2.0 g of 5 percent palladium on charcoal in 150 ml of glacial acetic acid was added 19.1 g of 1,2,3,4-tetrahydro-1-isonitroso-7-methoxynaphthalene. The mixture was treated with hydrogen at 40 pound per square inch (psi) with shaking in a Parr apparatus until the pressure dropped to 22 psi. The catalyst was removed by filtration and the acetic acid was removed by evaporation in vacuo. The residue was dissolved in methylene chloride and the solution was washed with 20 percent aqueous sodium hydroxide. The methylene chloride solution was then dried over anhydrous sodium sulfate. After removal of the drying agent by filtration, the solvent was removed by evaporation in vacuo to give 17.8 g of orange oil. The proton magnetic resonance spectrum was in accord with the structure of the product.

EXAMPLE 4

Preparation of N'-cyano-N-(7-methoxy-1,2,3,4-tetrahydro-1-naphthyl)-S-methylisothiourea, represented by the formula:

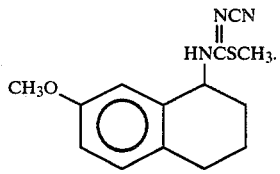

To a stirred solution of 17.8 g of 7-methoxy-1,2,3,4-tetrahydro-1-naphthylamine hydrochloride in 150 ml of ethanol at 0° C. was added 15.5 g of dimethyl cyanodithioiminocarbonate over a period of 30 minutes. The mixture was then allowed to remain at room temperature for 2 days after which the reaction mixture was cooled and the resulting crystals were collected by filtration. Concentration of the mother liquor gave a second crop of crystals. The combined product was recrystallized from ethanol to give 19.9 g of N'-cyano-N-(7-methoxy-1,2,3,4-tetrahydro-1-naphthyl)-S-methylisothiourea as colorless plates, mp 131°–132° C.

Analysis: Calcd for $C_{14}H_{17}N_3OS$: C, 61.06; H, 6.22; N, 15.26; S, 11.64.
Found: C, 61.2; H, 6.22; N, 15.31; S, 11.91.

EXAMPLE 5

Preparation of N''-cyano-N-ethyl-N'-(1,2,3,4-tetrahydro-1-naphthyl)guanidine, represented by the formula:

A solution of 6.13 g of N'-cyano-N-(1,2,3,4-tetrahydro-1-naphthyl)-S-methylisothiourea and 10 ml of 70 percent aqueous ethylamine in 90 ml of ethanol was heated at reflux with stirring for 20 hours. The reaction mixture was cooled in a refrigerator to give 2.44 g of N''-cyano-N-ethyl-N'-(1,2,3,4-tetrahydro-1-naphthyl)-guanidine as a white, crystalline solid, mp 152°–153.5° C.

| Analysis | C | H | N |
|---|---|---|---|
| Calculated for $C_{14}H_{18}N_4$: | 69.39 | 7.49 | 23.12 |
| Found: | 69.5 | 7.54 | 23.18 |

EXAMPLE 6

Preparation of N''-cyano-N-isopropyl-N'-(1,2,3,4-tetrahydro-1-naphthyl)guanidine, represented by the following formula:

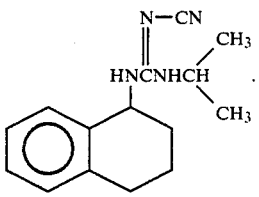

A solution of 30.0 g of N'-cyano-N-(1,2,3,4-tetrahydro-1-naphthyl)-S-methylisothiourea and 40 ml of isopropylamine in 300 ml of acetonitrile was heated at reflux with stirring for 154 hours. The solvent and excess isopropylamine were removed by evaporation in vacuo, leaving the crude product as a tacky, white solid. Crystallization from isopropyl acetate followed by a recrystallization from a mixture of isopropyl acetate and 2-propanol gave 5.13 g of N''-cyano-N-isopropyl-N'-(1,2,3,4-tetrahydro-1-naphthyl)guanidine as a white, crystalline solid, mp 170.5°–172.5° C.

| Analysis | C | H | N |
|---|---|---|---|
| Calculated for $C_{15}H_{20}N_4$: | 70.28 | 7.86 | 21.86 |
| Found: | 70.2 | 7.70 | 21.76 |

EXAMPLE 7

Preparation of N''-cyano-N-n-propyl-N'-(1,2,3,4-tetrahydro-1-naphthyl)guanidine, represented by the following formula:

A solution of 12.3 g of N'-cyano-N-(1,2,3,4-tetrahydro-1-naphthyl)-S-methylisothiourea and 16 ml of n-propylamine in 100 ml of acetonitrile was heated at reflux with stirring for 20 hours. The reaction mixture was then allowed to stand in a refrigerator to give 8.63 g of N"-cyano-N-n-propyl-N'-(1,2,3,4-tetrahydro-1-naphthyl)guanidine as a white, crystalline solid, mp 130.5°–131.5° C. A further quantity of the product was obtained by the concentration and subsequent cooling of the mother liquor.

| Analysis | C | H | N |
|---|---|---|---|
| Calculated for $C_{15}H_{20}N_4$: | 70.28 | 7.86 | 21.86 |
| Found: | 70.3 | 7.83 | 21.81 |

EXAMPLE 8

Preparation of N"-cyano-N-methyl-N'-(1,2,3,4-tetrahydro-1-naphthyl)guanidine, represented by the following formula:

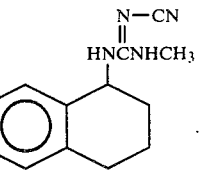

A solution of 12.3 g of N'-cyano-N-(1,2,3,4-tetrahydro-1-naphthyl)-S-methylisothiourea and 20 ml of 33 percent ethanolic methylamine in 200 ml of ethanol was heated at reflux with stirring for 22 hours. The solvent and excess methylamine were then removed by evaporation in vacuo, leaving the crude product as a glassy, amorphous solid. Crystallization from a mixture of isopropyl acetate, methylcyclohexane and 2-propanol gave 7.03 of N"-cyano-N-methyl-N"-(1,2,3,4-tetrahydro-1-naphthyl)guanidine as a white, crystalline solid, mp 169°–170° C.

| Analysis | C | H | N |
|---|---|---|---|
| Calculated for $C_{13}H_{16}N_4$: | 68.39 | 7.07 | 24.54 |
| Found: | 68.2 | 7.01 | 24.66 |

EXAMPLE 9

Preparation of N-allyl-N"-cyano-N'-(1,2,3,4-tetrahydro-1-naphthyl)guanidine, represented by the following formula:

A solution of 24.5 g of N"-cyano-N-(1,2,3,4-tetrahydro-1-naphthyl)-S-methylisothiourea and 38 ml of allylamine in 400 ml of ethanol was heated at reflux for 87 hours. The solvent was removed from the reaction mixture by evaporation in vacuo, leaving a pale yellow semisolid which was crystallized from isopropyl acetate to give 11.0 g of N-allyl-N"-cyano-N'-(1,2,3,4-tetrahydro-1-naphthyl)guanidine as a white, crystalline solid, mp 130°–132° C.

| Analysis | C | H | N |
|---|---|---|---|
| Calculation for $C_{15}H_{18}N_4$: | 70.84 | 7.13 | 22.03 |
| Found: | 70.83 | 7.15 | 22.14 |

EXAMPLE 10

Preparation of N"-cyano-N-n-butyl-N'-(1,2,3,4-tetrahydro-1-naphthyl)guanidine, represented by the formula:

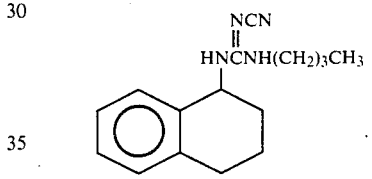

A solution of 12.3 g of N-cyano-N'-(1,2,3,4-tetrahydro-1-naphthyl)-S-methylisothiourea and 20 ml of n-butylamine in 100 ml of acetonitrile was heated at reflux with stirring for 100 hours. The solvent was removed by evaporation in vacuo. The residual oil was dissolved in methylene chloride, and the solution was washed with three 80 ml portions of 3N hydrochloric acid and then dried over anhydrous sodium sulfate. The methylene chloride was removed by evaporation in vacuo, leaving as residue N"-cyano-N-n-butyl-N'-(1,2,3,4-tetrahydro-1-naphthyl)guanidine as 9.73 g of a pale yellow, viscous oil.

Anal. Calcd for $C_{16}H_{22}N_4$: C, 71.07; H, 8.20; N, 20.72. Found: C, 70.8; H, 8.28; N, 20.63.

EXAMPLE 11

Preparation of N"-cyano-N-isobutyl-N'(1,2,3,4-tetrahydro-1-naphthyl)guanidine, represented by the formula:

A solution of 12.3 g of N-cyano-N'-(1,2,3,4-tetrahydro-1-naphthyl)-S-methylisothiourea and 20 ml of isobutylamine in 100 ml of acetonitrile was heated at reflux with stirring for 100 hours. The solvent was then removed by evaporation in vacuo. The residual oil was dissolved in methylene chloride and the solution was washed with three 80 ml portions of 3N hydrochloric acid and then dried over anhydrous sodium sulfate. The sodium sulfate was removed by filtration, and the methylene chloride was removed from the filtrate by evaporation in vacuo, leaving N''-cyano-N-isobutyl-N'-(1,2,3,4-tetrahydro-1-naphthyl)guanidine as 11.6 g of a pale yellow, viscous oil.

Anal. Calcd for $C_{16}H_{22}N_4$: C, 71.07; H, 8.20; N, 20.72. Found: C, 70.48; H, 8.05; N, 20.71.

EXAMPLE 12

Preparation of N-tert.-butyl-N''-cyano-N'-(1,2,3,4-tetrahydro-1-naphthyl)guanidine, represented by the formula:

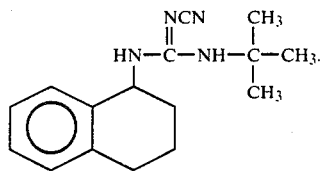

A solution of 5.0 g of N-tert.-butyl-N'-cyano-S-methylisothiourea (the urea compound was prepared by the method of J. W. Tilley and H. Ramuz, Helv. Chim. Acta 63, 832 (1980)) and 5.0 g of 1,2,3,4-tetrahydro-1-naphthylamine in 100 ml of acetonitrile was heated at reflux for two weeks. The solvent was then removed by evaporation in vacuo. The residue was dissolved in methylene chloride and the solution washed with 3N hydrochloric acid and dried over anhydrous sodium sulfate. After removing the drying agent by filtration, the methylene chloride was removed by evaporation in vacuo, leaving an oil, which was purified by column chromatography on silica gel, using ethyl acetate as eluent. The ethyl acetate was then removed by evaporation, and the residue was crystallized from a mixture of ethyl ether and hexane, to give N-tert.-butyl-N''-cyano-N'-(1,2,3,4-tetrahydro-1-naphthyl)guanidine as 6.2 g of a white, crystalline solid, mp 123°–126°.

Anal. Calcd for $C_{16}H_{22}N_4$: C, 71.07; H, 8.20; N, 20.73. Found: C, 71.1; H, 8.21; N, 20.80.

EXAMPLE 13

Preparation of N''-cyano-N-cyclopropyl-N'-(1,2,3,4-tetrahydro-1-naphthyl)guanidine, represented by the formula:

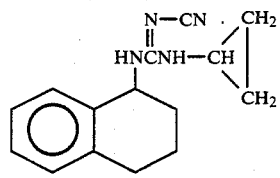

A solution of 24.6 g of N'-cyano-N-(1,2,3,4-tetrahydro-1-naphthyl)-S-methylisothiourea and 25.0 g of cyclopropylamine in 250 ml of ethanol was heated at reflux with stirring for ca. 120 hours. The solvent was then removed by evaporation in vacuo. The residual oil was dissolved in a mixture of hot isopropyl acetate and ethanol, and the solution was allowed to stand in the refrigerator overnight to give the partially-purified product as a white, crystalline solid. A further quantity of the crude product was obtained by the concentration and subsequent cooling of the mother liquor. Recrystallization from isopropyl acetate, containing a small amount of ethanol, gave N''-cyano-N-cyclopropyl-N'-(1,2,3,4-tetrahydro-1-naphthyl)guanidine as 7.75 g of a white, crystalline solid, mp 170.5°–171.5° C.

Anal. Calcd for $C_{15}H_{18}N_4$: C, 70.84; H, 7.13; N, 22.03. Found: C, 70.6; H, 7.06; N, 22.07.

EXAMPLE 14

Preparation of N''-cyano-N-ethyl-N'-(1,2,3,4-tetrahydro-7-methoxy-1-naphthyl)guanidine, represented by the formula:

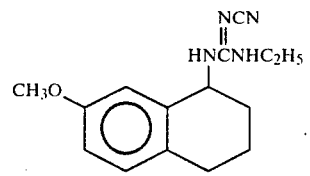

A solution of 5.5 g of N-cyano-N'-(1,2,3,4-tetrahydro-7-methoxy-1-naphthyl)-S-methylisothiourea and 10 ml of 70 percent aqueous ethylamine in 100 ml of ethanol was heated at reflux for 37 hours. The solvent was removed by evaporation in vacuo, and the residue was chromatographed on silica gel, using ethyl acetate as eluent. The ethyl acetate was removed from the eluate by evaporation in vacuo, and the residue was crystallized from toluene to give N''-cyano-N-ethyl-N'-(1,2,3,4-tetrahydro-7-methoxy-1-naphthyl)guanidine as 2.7 g of white, crystalline solid, mp 130°–131°.

Anal. Calcd for $C_{15}H_{20}N_4O$: C, 66.15; H, 7.40; N, 20.57. Found: C, 66.4; H, 7.31; N, 20.33.

EXAMPLE 15

In representative pre-emergence operations, seeds of various plants are planted in seed beds and, while exposed, sprayed with compositions containing an active compound. The treated seeds are then covered with a layer of soil and the test beds maintained under conditions conducive to growth for a period of about 14 days. The test compositions are prepared by procedures known in the art and/or described herein. For simplicity, the various plants used for pre-emergence testing are designated by abbreviations as shown in Table 1. Representative results of the pre-emergent testing are shown in Table 2.

TABLE 1

| Abbreviations used for Plants | |
| --- | --- |
| Plant | Abbreviation |
| Nutsedge | NS |
| Pig Weeds | PW |
| Soybean | SO |
| Cotton | CO |
| White Winter Wheat | WW |
| Crabgrass | CR |
| Corn | CN |
| Sorghum/Milo | SM |
| Johnson Grass | JG |
| Barnyard Grass | BG |
| Sugar Beets | SB |
| Wild Oats | WO |
| Yellow Foxtail | YF |
| Rape | RA |
| Cultured Rice | RI |
| Velvet Leaf | VL |
| Jimson Weed | JW |
| Morning Glory | MG |
| Tomato | TO |
| Water Grass | WG |

TABLE 2

Pre-emergent Herbicidal Test Results

| Compound of Example Number | Application Rate (pounds/acre) | NS | PW | SO | CO | WW | CR | CN | SM | JG | BG | SB | WO | YF | RA | RI | VL | JW | MG | TO | WG |
|---|---|---|---|---|---|---|---|---|---|---|---|---|---|---|---|---|---|---|---|---|---|
| 1 | 0.25 | NT* | 30 | NT | NT | NT | NT | NT | NT | NT | NT | 0 | NT | NT | 0 | NT | NT | 10 | NT | NT | NT |
|   | 2.00 | 0 | 100 | 10 | 30 | NT | NT | 20 | 20 | 95 | 40 | 100 | NT | 50 | 70 | 20 | 100 | 100 | NT | NT | NT |
|   | 4.00 | 10 | 100 | 30 | 70 | 0 | 40 | 80 | 40 | 100 | 95 | 100 | 0 | 80 | 100 | 40 | 100 | 100 | NT | NT | 0 |
| 4 | 0.25 | NT | NT | 97 | NT | NT | NT | NT | NT | 80 | NT | 0 | NT | 40 | NT | NT | 0 | 100 | 90 | 20 | 70 |
|   | 2.00 | 20 | NT | 100 | NT | 0 | NT | 20 | 0 | 93 | NT | 100 | 30 | 100 | 50 | 50 | 70 | 100 | 70 | 100 | 100 |
|   | 10.00 | NT | 100 | NT | 90 | NT | 100 | NT | NT | NT | NT | NT | 100 | 100 | NT | NT | 100 | 100 | 98 | 100 | NT |
| 5 | 0.25 | NT | 95 | NT | NT | NT | NT | NT | 60 | NT | 70 | 10 | NT | 95 | 0 | 0 | 20 | 20 | NT | NT | NT |
|   | 2.00 | 10 | 100 | 30 | 30 | 0 | 100 | 40 | 98 | NT | 98 | 100 | 0 | 100 | 80 | 30 | 100 | 100 | 80 | NT | 0 |
|   | 4.00 | 20 | 100 | 70 | 100 | NT | 100 | 50 | NT | 95 | NT | 100 | NT | NT | 100 | NT | NT | NT | NT | NT | 90 |
| 6 | 0.25 | NT | 90 | 40 | 70 | 20 | 0 | 0 | 0 | 95 | NT | 40 | 0 | 98 | 98 | 30 | 100 | 100 | 40 | NT | 100 |
|   | 2.00 | NT | 100 | NT | 95 | NT | 100 | 50 | 95 | NT | 100 | NT | 20 | 100 | NT | NT | 100 | NT | 20 | NT | NT |
|   | 10.00 | NT | 100 | NT | 98 | NT | 100 | NT | NT | NT | NT | NT | 100 | 100 | NT | NT | 100 | NT | 100 | NT | 0 |
| 7 | 10.00 | NT | 100 | NT | NT | NT | NT | NT | NT | NT | NT | NT | NT | 100 | NT | NT | 10 | 0 | NT | NT | 10 |
| 8 | 0.25 | NT | NT | 0 | 0 | 0 | 0 | 0 | 0 | 0 | NT | 0 | 0 | 0 | 0 | 0 | 40 | 20 | 0 | NT | 40 |
|   | 0.50 | NT | NT | NT | 30 | NT | NT | NT | NT | 10 | NT | NT | NT | 20 | NT | NT | 90 | 60 | NT | NT | 0 |
|   | 1.00 | 0 | NT | 70 | 10 | 0 | NT | 0 | 0 | 0 | NT | 40 | 0 | 60 | 20 | 0 | 50 | 30 | NT | 10 | 60 |
| 9 | 0.50 | NT | NT | NT | 70 | 60 | NT | 50 | 30 | 90 | NT | 95 | NT | 70 | 100 | NT | 100 | 100 | 20 | 90 | 40 |
|   | 2.00 | NT | NT | 90 | NT | NT | NT | NT | NT | 99 | NT | 100 | 0 | 85 | 100 | NT | 100 | 100 | 60 | 100 | NT |
|   | 4.00 | 0 | NT | NT | 40 | NT | 100 | NT | NT | NT | 100 | NT | 100 | 100 | NT | NT | 100 | NT | 60 | NT | NT |
| 10 | 10.00 | NT | 100 | NT | NT | NT | 100 | NT | NT | NT | NT | NT | 100 | 100 | NT | NT | 100 | NT | 100 | NT | NT |
| 11 | 10.00 | NT | 100 | NT | NT | NT | 100 | NT | NT | 50 | NT | NT | 100 | 100 | NT | NT | 100 | NT | 100 | NT | 60 |
| 12 | 0.25 | NT | NT | 0 | 40 | 0 | 98 | 30 | 0 | 95 | NT | 0 | 40 | 90 | 0 | 10 | 30 | 50 | 0 | 0 | 80 |
|   | 2.00 | NT | 100 | 100 | 80 | NT | NT | NT | NT | NT | NT | NT | 50 | 80 | NT | NT | 97 | NT | 80 | NT | 80 |
|   | 10.00 | NT | 100 | NT | NT | NT | NT | NT | NT | NT | NT | NT | NT | NT | NT | NT | NT | NT | NT | NT | NT |
| 13 | 0.25 | NT | NT | NT | 0 | NT | NT | 0 | NT | 0 | NT | 0 | NT | 50 | 0 | 0 | 0 | 0 | 0 | NT | 0 |
|   | 2.00 | NT | 100 | 10 | 20 | 0 | NT | 20 | NT | 100 | NT | 100 | NT | 50 | 50 | NT | 60 | 70 | 100 | NT | 100 |
|   | 10.00 | NT | NT | NT | NT | NT | NT | NT | NT | NT | NT | NT | NT | 100 | NT | NT | 100 | NT | NT | NT | NT |
| 14 | 0.25 | 0 | NT | 50 | 0 | 10 | NT | 70 | 70 | 90 | NT | 100 | 60 | 60 | 100 | 60 | 60 | 100 | 50 | 100 | 80 |
|   | 2.00 | NT | 100 | NT | 100 | NT | 100 | NT | NT | NT | NT | NT | 100 | 100 | NT | NT | 100 | NT | 100 | NT | 100 |

*NT = Not tested

EXAMPLE 16

Representative compositions of the present invention were evaluated to determine their effectiveness in postemergent operations.

Aqueous dispersions were prepared by admixing one of the hereinafter set forth compounds, dissolved in a predetermined amount of an inert solvent with a predetermined quantity of water and a predetermined amount of a surfactant to give aqueous dispersions of one of the compounds as the sole toxicant.

Various plant species were planted in beds of good agricultural soil and grown in a greenhouse. After the plants had emerged and had grown to a height of from 2-8 inches (depending on the plant species), separate beds of the plants were sprayed to run-off with one of the above-prepared compositions at a treating concentration of from 15.6 to 4,000 parts per million (ppm). Other beds were treated only with a water-surfactant mixture, containing no active compound, to serve as controls. After treatment, the beds were maintained for about two weeks under greenhouse conditions conducive for good plant growth. At the end of this period, the beds were examined to determine the amount of kill and control.

Table 3 lists each specific compound that was found to give from substantial to complete control (i.e., from about 70 to about 100 percent when the compound was applied in a solution of about 500 to 4,000 ppm of specific compound) of the plant species listed immediately after said compound.

TABLE 3
Post-emergent Herbicidal Results

| Compound of Example Number | Plants Controlled |
| --- | --- |
| 4 | Morning Glory, Pig Weeds, Soybeans, Cotton, Crabgrass, Johnson Grass, Velvet Leaf, Sugar Beets, Water Grass, Wild Oats, Foxtail, Yellow Foxtail, Cocklebur Jimson Weed |
| 5 | Johnson Grass, Barnyard Grass, Sugar Beets, Cocklebur, Lambsquarter, Pennsylvania Smartweed, Pigweeds, Yellow Foxtail, Crabgrass |
| 6 | Pigweeds, Crabgrass, Velvet Leaf, Jimson Weed |
| 7 | Cotton, Pigweed, Crabgrass, Yellow Foxtail, Velvet Leaf, Wild Oats |
| 8 | Pigweeds, Cotton, Crabgrass, Johnson Grass, Sugar Beets, Rape, Cocklebur, Velvet Leaf, Jimson Weed |
| 10 | Cotton, Pigweed, Crabgrass, Yellow Foxtail, Velvet Leaf, Wild Oats |
| 11 | Cotton, Pigweed, Crabgrass, Yellow Foxtail, Velvet Leaf, Wild Oats, Barnyard Grass |
| 12 | Pigweeds, Crabgrass, Sugar Beets, Water Grass, Wild Oats, Foxtail, Yellow Foxtail, Rape, Velvet Leaf |
| 13 | Pigweeds, Crabgrass, Sugar Beets, Water Grass, Yellow Foxtail, Velvet Leaf, Jimson Weed |
| 14 | Pigweeds, Soybean, Crabgrass, Sugar Beets, Water Grass, Foxtail, Rape, Cocklebur, Velvet Leaf, Jimson Weed, Morning Glory |

Methods of Application

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is typically anionic or nonionic, and suitable absorptive grinding aids are typically of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the members of the group known to the art as wetting agents and emulsifiers are suitable.

Dust carriers may be micaceous talcs, pyrophyllite, dense kaolin clays, tobacco dust, ground calcium phosphate rock, and the like.

Grinding aids may be attapulgite clay, diatomaceous silica, synthetic fine silica, synthetic calcium and magnesium silicates, and the like.

Although the proportions of ingredients are not known to be critical, the inert solid carriers in the dusts of this invention may be present in concentrations of from about 30 to 90 weight percent of the total composition. The grinding aid may constitute 5 to 50 weight percent of the compositions, and the wetting agent may constitute from about 0 to 1.0 weight percent of the composition. Dust compositions can also contain other surfactants such as dispersing agents, and minor amounts of anticaking and antistatic agents. The particle size of the carrier is not known to be critical, but may be in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Such emulsifying agents typically comprise from about 1 to 10 weight percent of the total composition.

Thus, emulsifiable concentrates of the present invention typically comprise from about 15 to about 50 weight percent active material, about 40 to 82 weight percent solvent, and about 1 to 10 weight percent emulsifier. Other additives such as spreading agents and the like can also be included.

C. GRANULES AND PELLETS

Granules and pellets are physically stable, particulate compositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is typically of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations typically up to about 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with about 25 to 30 weight percent active component, but more frequently a concentration of about 10 weight percent is desired for optimum distribution. The granular compositions of this invention are typically most useful in a size range of 15-30 mesh.

The surfactant is generally a common wetting agent of anionic or nonionic character. The most suitable wetting agents depend upon the type of granule used. Such wetting agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage a solid, powdered anionic wetting agent. Such agents will typically comprise from about 0 to 2 weight percent of the total composition.

Thus, typical granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95 percent of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 ml in diameter. Granules formed by extrusion, agglomeration, or prilling may be useful in the present invention as well as materials in their naturally occurring form. Examples of such carriers are vermiculite, sintered clay granules, kaolin, attapulgite clay, sawdust, and granular carbon.

E. IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient typically varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A method for controlling the growth of plants comprising applying to said plants or plant loci a herbicidally effective amount of a compound of the formula:

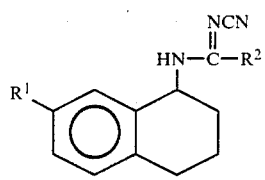

wherein $R^1$ is hydrogen or methoxy; and $R^2$ is methylthio; alkylamino of the formula:

wherein $R^3$ is a straight chain, branched, or cyclic alkyl moiety of 1 to 12 carbon atoms; or alkenylamino of the formula

wherein $R^4$ is a straight chain or branched alkenyl moiety of 3 to 12 carbon atoms.

2. The method of claim 1, wherein said compound is

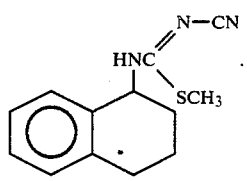

3. The method of claim 1, wherein said compound is

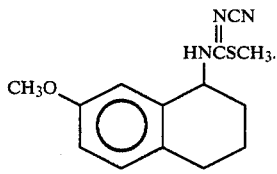

4. The method of claim 1, wherein said compound is

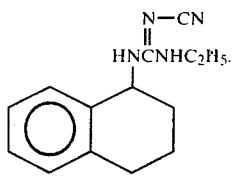

5. The method of claim 1, wherein said compound is

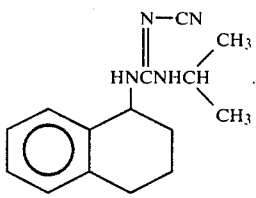

6. The method of claim 1, wherein said compound is

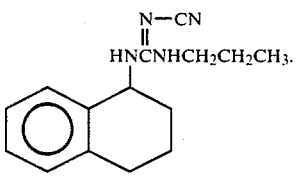

7. The method of claim 1, wherein said compound is

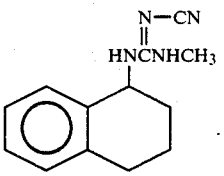

8. The method of claim 1, wherein said compound is

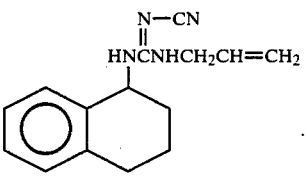

9. The method of claim 1, wherein said compound is

10. The method of claim 1, wherein said compound is

11. The method of claim 1, wherein said compound is

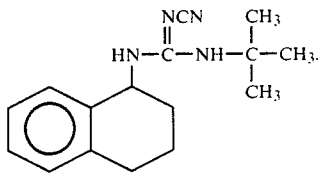

12. The method of claim 1, wherein said compound is

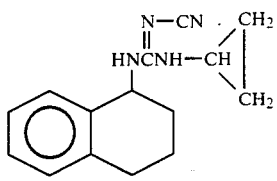

13. The method of claim 1, wherein said compound is

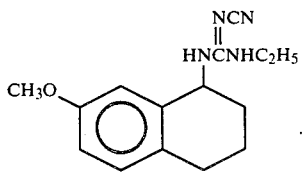

14. A herbicidal composition comprising a herbicidally effective amount of a compound of the formula:

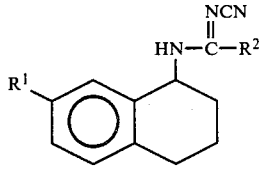

wherein $R^1$ is hydrogen or methoxy; and $R^2$ is methylthio; alkylamino of the formula:

—NH—$R^3$ wherein $R^3$ is a straight chain, branched, or cyclic alkyl moiety of 1 to 12 carbon atoms, or alkenylamino of the formula:

—NH—$R^4$ wherein $R^4$ is a straight chain or branched alkenyl moiety of 3 to 12 carbon atoms, and an inert diluent carrier.

15. The composition of claim 14, wherein said compound is

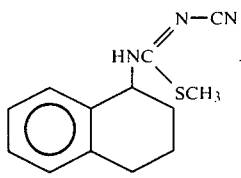

16. The composition of claim 14, wherein said compound is

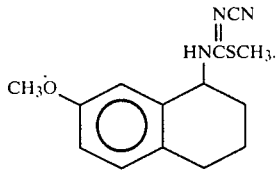

17. The composition of claim 14, wherein said compound is

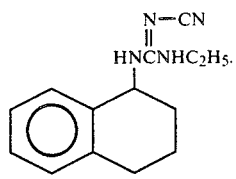

18. The composition of claim 14, wherein said compound is

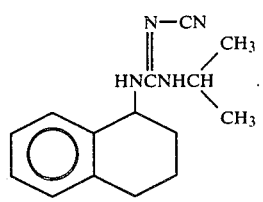

19. The composition of claim 14, wherein said compound is

20. The composition of claim 14, wherein said compound is

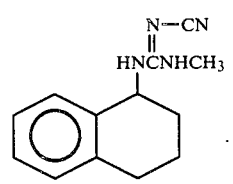

21. The composition of claim 14, wherein said compound is
22. The composition of claim 14, wherein said compound is
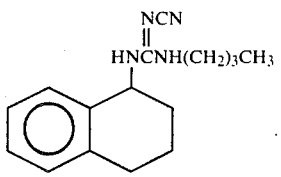
23. The composition of claim 14, wherein said compound is
24. The composition of claim 14, wherein said compound is
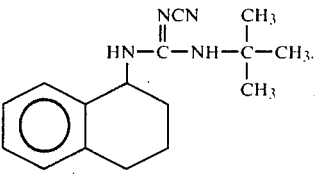
25. The composition of claim 14, wherein said compound is
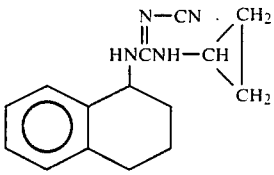
26. The composition of claim 14, wherein said compound is
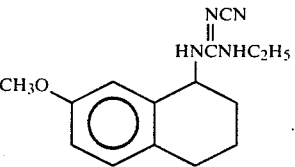
* * * * *